United States Patent [19]

Snipes et al.

[11] Patent Number: 4,832,955
[45] Date of Patent: May 23, 1989

[54] CONTROLLED RELEASE POTASSIUM CHLORIDE COMPOSITION

[75] Inventors: Wallace C. Snipes; Stephen J. Wagner, both of Centre County, Pa.

[73] Assignee: Zetachron, Inc., State College, Pa.

[21] Appl. No.: 160,735

[22] Filed: Feb. 26, 1988

[51] Int. Cl.$^4$ .............................................. A61L 9/64
[52] U.S. Cl. ..................................... 424/456; 424/495
[58] Field of Search ............... 514/263, 269, 253, 489; 424/44, 495, 468, 469, 470, 456

[56] References Cited

U.S. PATENT DOCUMENTS 3,960,757  6/1976  Morishita et al. .................. 424/497
4,713,248  12/1987  Kjornaes et al. .................. 424/469

Primary Examiner—Thurman K. Page
Attorney, Agent, or Firm—Smith & Schnacke

[57] ABSTRACT

The invention is directed to a pharmaceutical composition comprising a microencapsulated potassium salt encapsulated in a shell wall consisting essentially of from about 85% to about 97% ethyl cellulose and from about 3% to about 15% of an amphiphile based on the weight of the shell wall; wherein the weight of said shell wall is from about 3% to about 15% of the total weight of the microencapsulated potassium salt.

18 Claims, No Drawings

CONTROLLED RELEASE POTASSIUM CHLORIDE COMPOSITION

BACKGROUND OF THE INVENTION

Potassium is an essential element for maintaining health in animals and humans. Potassium ions participate in a number of essential physiological processes, including the maintenance of intracellular tonicity, the transmission of nerve impulses, the contraction of muscles and the maintenance of normal renal functions. Potassium is the predominating cation of intracellular fluids and erythrocytes.

Potassium depletion or potassium deficiency, also known as hypokolemia, can be induced in an animal or human in a variety of ways. Potassium depletion can occur whenever the rate of potassium loss through renal excretion and/or loss from the gastrointestinal tract exceeds the rate of potassium intake. Such depletion usually results slowly as a consequence of prolonged therapy with oral diuretics, primary or secondary hyperaldosteronism, diabetic ketoacidosis, severe diarrhea or inadequate replacement of potassium in patients on prolonged parenteral nutrition.

Potassium depletion due to these causes is usually accompanied by a deficiency of chloride ions. Both such deficiencies could be alleviated if potassium chloride was administered to the human or animal. Further, the most convenient mode of such administration would be to give the human or animal a potassium chloride tablet to ingest orally.

Unfortunately, potassium chloride tablets have been known to produce stenotic and/or ulcerative lesions of the small bowel and deaths, in addition to upper gastrointestinal bleeding. These lesions are caused by high localized concentrations of potassium ion in the region of a rapidly dissolving tablet which injures the bowel wall and thereby produces obstruction, hemorrhage, or perforation.

U.S. Pat. No. 2,921,883 describes the preparation of a wax-matrix solid dosage form of potassium chloride. Although fewer bowel lesions have been observed with wax-matrix tablets compared to enteric coated tablets there are still drawbacks to the use of wax-matrix tablets. The rate of dissolution of the potassium chloride from the matrix may be uneven resulting in large amounts of potassium and chloride ions being released at one time. Wax matrix tablets may tend to lay in one spot in the intestine. It is known that wax-matrix potassium chloride preparations have produced esophageal ulceration in certain cardiac patients with esophogeal compression due to an enlarged left atrium. *Physicians' Desk Reference* ®(1987), p. 1629, Medical Economics Company Inc., Oradel, NJ 07649.

One way of overcoming the harmful side effects associated with administration of solid potassium chloride is to administer potassium chloride in an aqueous solution. However, there are distinct disadvantages associated with liquid pharmaceutical products. For example, the finished dosage form, i.e., the product which sits on the pharmacy shelf takes up more space than a tablet. Liquids may not be convenient to take for the ambulatory working patient, and breaking and leakage of the container could present a problem. More importantly, liquids tend to be bad tasting and the patient may not take the liquid potassium according to the prescribed doseage schedule.

Effervescent potassium chloride compositions are taught by U.S. Pat. No. 3,903,255. This '255 patent also describes the problems associated with such compositions. Often times an unappetizing scum is formed in solutions prepared from the effervescent tablets. Also, quite often, the effervescent powder does not completely go into solution leaving partially dissolved potassium chloride residue which is difficult for the human or animal to swallow apart from the rest of the liquid.

It is therefore highly desirable to have a solid-dosage form of potassium chloride which does not contain the inherent problems of the prior art tablet, liquid, and effervescent forms described above, yet is conveniently administered as an oral-dosage form.

One such oral-dosage form is a capsule containing microencapsulated potassium salt. Such dosage form is described in U.S. Pat. No. 4,259,315. The '315 patent discloses pharmaceutical compositions suitable for oral administration to monogastric animals consisting of gelatin capsules containing mixtures of microencapsulated potassium salt and a hydrophyllic surfactant external to the microcapsules.

As taught by the '315 patent, microencapsulation in ethyl cellulose shell walls is old in the art. Further, potassium chloride encapsulated with a film of ethyl cellulose is known. U.S. Pat. No. 3,415,758 describes the preparation of microencapsulated potassium chloride via phase separation or coacervation techniques. These microcapsules may also be prepared according to an an air suspension coating process similar to the Wurster air suspension process described in U.S. Pat. Nos. 3,117,027; 3,196,827; 3,241,250 and 3,253,944.

U.S. Pat. No. 4,389,331 describes the preparation of ethyl cellulose microcapsules containing a pharmaceutically active compound by phase separation coacervation where phospholipids are used as a phase-separation inducing agent. U.S. Pat. Nos. 4,411,933 and 4,486,471 describes a similar processes.

There are however, disadvantages associated with the administration of gelatin capsules containing microcapsules having ethyl cellulose shell walls. The microencapsulated potassium chloride can agglomerate during the dissolution of the gelatin capsule. This greatly increases the possibility that the clump of microencapsulated potassium chloride will remain in one spot of the gastrointestinal tract and thus, release high concentrations of potassium and chloride ions which can cause ulceration or lesions.

Surprisingly, it has been found that microcapsules of the invention having shell walls formed of a combination of ethyl cellulose and long chain fatty acid do not tend to agglomerate in the gastrointesinal tract yet still release potassium chloride at the same rate as microcapsules having shell walls formed only of ethyl cellulose. The microcapsules of the invention disperse rapidly in both gastric and intestinal fluids and the shell walls of the invention are stronger than shell walls of ethyl cellulose alone. The microcapsules of the invention are more uniformly spherical than prior art microencapsulated potassium chloride.

SUMMARY OF THE INVENTION

The invention is directed to a pharmaceutical composition comprising microencapsulated potassium salt encapsulated in a shell wall containing essentially of from about 85.0% to about 97.0% ethyl cellulose and from about 3.0% to about 15.0% of an amphiphile based on the weight of the shell wall; wherein the weight of said shell wall is from about 3% to about 15% of the total weight of said microencapsulated potassium salt. Preferably the pharmaceutical composition of the invention is filled into gelatin capsules for ease of administration to an animal or a human.

DETAILED DESCRIPTION OF THE INVENTION

The present invention is directed to a pharmaceutical composition comprising a microencapsulated potassium salt as the active agent wherein the microcapsule shell wall consists essentially of from about 85.0% to about 97.0% ethylcellulose and from about 3.0% to about 15.0% of an amphiphile based on the weight of the shell wall; wherein the weight of said shell wall is from about 3% to about 15% of the total weight of said microencapsulated potassium salt.

As used herein the term "potassium salt" refers to any potassium salt which adequately provides potassium cations to the animal or human being treated and which may be taken internally. Suitable potassium salts are potassium chloride, potassium iodide, potassium gluconate, potassium acetate, potassium citrate, potassium sodium tartrate, potassium phosphate and the like. The preferred potassium salt for use herein is potassium chloride since this salt provides desirable chloride ions as well as potassium ions.

The potassium salt makes up about 85% to about 97% of the weight of the microencapsulated potassium of the invention. Preferably, the potassium salt will make up about 85% to about 95% of the total weight and more preferably about 89% to about 91% of the total weight of the microencapsulated salt. The shell wall forms about 3% to about 15% of the total weight of the microencapsulated potassium salt, preferably about 7% to about 13% of the total weight and more preferably from about 8.5% to about 9.5% of the total weight of the microencapsulated potassium.

The microcapsule shell wall is made up of from about 85% to about 97% of ethyl cellulose; preferably from about 85% to about 95% and more preferably from about 89% to about 91% of ethyl cellulose. The remainder of the weight of the microcapsule shell wall is from the water-insoluble amphiphile which makes up from about 3.0% to about 15% of the shell wall, preferably from about 5% to about 15% and more preferably from about 8.5% to about 9.5% of the microcapsule shell wall.

As used herein the term "amphiphile" refers to a water-insoluble material whose molecule possesses a hydrophilic portion and a lipophilic portion usually located at opposite ends of a relatively elongated molecule. Suitable amphiphiles for use in the present invention are $C_{12}$-$C_{20}$ fatty acids such as lauric acid, myristic acid, palmitic acid, stearic acid, and arachidic acid; $C_{12}$-$C_{20}$ alcohols such as lauryl alcohol, myristyl alcohol, stearyl alcohol, and the like and $C_{12}$-$C_{20}$ fatty acid esters. U.S. Pat. No. 4,629,621, at Col. 3, lines 16-19 and Col. 4, lines 1-5 provides a description of such useful amphiphiles.

The microcapsules of the present invention are prepared according to techniques well known in the art. The microcapsules of the invention are prepared as follows: ethyl cellulose and the water-insoluble amphiphile are dissolved in a suitable solvent for both materials and the solution is stirred. Thereafter, the appropriate amount of the potassium salt preferably in the form of beads or crystals, is coated with the solution by spraying in a fluidized bed according to procedures well known in the art to produce microencapsulated potassium salt. The use of a fluidized bed in an air suspension coating process is described in U.S. Pat. Nos. 3,117,027; 3,196,827; 3,241,250 and 3,253,944.

The microcapsules of the invention are from about 250 microns to about 700 microns in diameter with most being about 300-600 microns in diameter. The microencapsulated potassium salts of the present invention are free-flowing, relatively spherical capsules which do not tend to agglomerate in intestinal fluid as do the prior art ethyl cellulose microcapsules.

Suitable solvents for use in the process described herein are for example, solvents which are known to be useful for producing ethyl cellulose microcapsules. Any solvent which will dissolve ethyl cellulose and the amphiphile can be used as a solvent in the process described herein. Examples of such solvents are cyclohexane, mixtures of cyclohexane and n-hexane, methylene chloride, and the like. The preferred solvent for use herein is methylene chloride.

The microcapsules of the present invention are preferably prepared by an air suspension coating technique, such as the Wurster air suspension coating process disclosed in U.S. Pat. Nos. 3,117,027; 3,196,827; 3,241,520 and 3,253,944. In this process, potassium salt beads are fluidized in a bed while a solution or suspension of ethyl cellulose and fatty acid in a volatile organic solvent for example, methylene chloride is sprayed into the bed. As droplets of this spray deposit upon the potassium salt bead the solvent evaporates and a coating builds up on the potassium salt bead. The final size of the microcapsules is determined by the size of the fluidized potassium salt bead plus the weight of the coating applied to said potassium salt. It is desirable, although not essential, to prescreen the potassium salt before the salt is fluidized so as to start off with beads or crystals of relatively uniform particle size. The potassium salt bead is preferably reduced to a less than 40-60 mesh size before being coated.

The following examples illustrate in detail the preparation of the microcapsules of the invention and their release rate. These examples are illustrative and are not meant to limit the scope of the invention.

EXAMPLE 1

Ethyl Cellulose/Palmitic Acid Shell Wall

To 900 mL of methylene chloride was added 60 g of ethyl cellulose and 6 g of palmitic acid. The mixture was stirred to form a solution. The resulting solution was sprayed slowly onto 650 g potassium chloride beads (30-40 mesh) in a Uniglatt ® brand laboratory scale fluidized bed using pressurized air (2 atm). The spraying rate was about 30 mL/min and the air temperature in the fluidized bed was 40° C. The resulting microcapsules were about 400 to about 600 microns in diameter. The microcapsules were free-flowing, relatively spherical, particles.

The microencapsulated potassium salt of the invention was tested in the standard test procedure for determining dissolution (release) rate from solid dosage forms like tablets or capsules to determine the release properties.

EXAMPLE 2

Dissolution Test Procedure

The test procedure and apparatus for carrying out the Dissolution Test was as described in THE UNITED STATES PHARMACOPEIA 21st Rev. (1984), pp. 1243-1244, United States Pharmocopeial Convention, Inc., Rockville, MD 20852. In these tests, Apparatus 2 with the paddle stirring element was used. The release of potassium salt from the microcapsules was measured by following the appearance of potassium ion ($K^+$) in the Dissolution Medium using a potassium ion electrode (ORION Model 93-19), and appropriate potassium chloride reference solutions. The composition of the medium used in these tests is as follows:

1. Simulated Gastric Fluid Lacking Pepsin (SGF)

Dissolve 2.0 g of sodium chloride in 7.0 mL of hydrochloride acid and add sufficient water to make 1000 mL. The pH of the solution will be about 1.2.

2. Simulated Intestinal Fluid Lacking Pancreatin (SIF)

Dissolve 6.8 g of monobasic sodium phosphate in 250 mL of water with stirring. To the solution is added 190 mL of 0.2N sodium hydroxide and 400 mL of water. To the resulting solution is added sufficient 0.2N sodium hydroxide to adjust pH of solution of 7.5±0.1. Thereafter, sufficient water is added to the solution to bring the volume to 1000 mL.

A portion (5 g) of the microcapsules of potassium chloride from Example 1 was added to 900 mL of SIF and the dissolution of potassium from the microcapsule was observed over time. The results are summarized in Table 1.

TABLE 1

| Time | % $K^+$ Released |
|---|---|
| 1 | 15 |
| 2 | 30 |
| 3 | 44 |
| 4 | 57 |
| 6 | 78 |
| 8 | 91 |
| 10 | 96 |
| FIN | 100 |

EXAMPLE 3

Microcapsules were prepared as described in Example 1, except that 500 g of 30/40 mesh KCl was encapsulated using a solution of 45 g of ethyl cellulose and 5 g of myristic acid dissolved in 750 mL of methylene chloride. A sample of the microcapsules were tested according to the Dissolution Test Procedure of Example 2. The results are summarized in Table 2.

TABLE 2

| Time | % $K^+$ Released | |
|---|---|---|
| (hr.) | SIF | SGF |
| 1 | 19 | 19 |
| 2 | 36 | 37 |
| 3 | 51 | 53 |
| 4 | 68 | 67 |
| 6 | 89 | 87 |
| 8 | 94 | 94 |
| 10 | 98 | 100 |
| 12 | 102 | 102 |
| FIN | 100 | 100 |

EXAMPLE 4

Utilizing the procedure described in Example 1, microencapsulated potassium chloride was prepared with shell walls having the following composition expressed as % of total weight of microencapsulated potassium:

| | Sample | | |
|---|---|---|---|
| Component | 1 | 2 | 3 |
| Ethyl Cellulose | 8.2 | 9.1 | 9.1 |
| Myristic Acid | 0.91 | — | — |
| Palmitic Acid | — | 0.91 | — |
| Stearyl Alcohol | — | — | 0.91 |

Samples of each of these microcapsules were stored at room temperature and at 45° C. for 9 weeks. The results are summarized in Table 3.

TABLE 3

| | % $K^+$ Released In SIF | | | | | | | | |
|---|---|---|---|---|---|---|---|---|---|
| | Sample 1 | | | Sample 2 | | | Sample 3 | | |
| Time (hr.) | [1]IN | [2]RT | 45° C. | IN | RT | 45° C. | IN | RT | 45° C. |
| 1 | 17 | 17 | 9 | 10 | 10 | 10 | 20 | 26 | 20 |
| 2 | 35 | 35 | 41 | 27 | 25 | 31 | 40 | 51 | 51 |
| 4 | 67 | 85 | 80 | 57 | 55 | 63 | 65 | 75 | 81 |
| 6 | 85 | 90 | 77 | 77 | 77 | 71 | 81 | 81 | 81 |
| 8 | 93 | 93 | 93 | 90 | 90 | 75 | 90 | 90 | 90 |
| 10 | 99 | 99 | 99 | 97 | 98 | 90 | 100 | 100 | 100 |
| 12 | 100 | 100 | 100 | 100 | 100 | 100 | 100 | 100 | 100 |

[1]IN = Initial dissolution rate
[2]RT = Room Temperature

The data presented in Table 3 illustrates that the microcapsules of the present invention are stable over time and that even under conditions of accelerated aging (9 wks at 45° C.) the microcapsules of the invention have a dissolution pattern very similar to freshly prepared microcapsules.

EXAMPLE 5

Microcapsules having shell walls of only ethyl cellulose were prepared as described in Example 1, except that 50 g of ethyl cellulose was dissolved in 700 mL of methylene chloride and sprayed on to 500 g of 30/40 mesh potassium chloride beads. The dissolution rate of the invention microcapsules of Example 1 having a shell wall of ethyl cellulose/palmitic acid were compared to the dissolution rate of the microcapsules of this example have only ethyl cellulose shell walls. The results of the Dissolution Test are summarized in Table 4.

TABLE 4

| | % $K^+$ Released Shell Wall Type | |
|---|---|---|
| Time (hr.) | Et Cell | Et Cell/Palm. |
| 1 | 20 | 14 |
| 2 | 40 | 40 |
| 4 | 75 | 75 |
| 6 | 87.5 | 95 |
| 8 | 95 | 97.5 |

As illustrated by the data summarized in Table 4, when the release kinetics were compared for microcapsules having a shell wall of ethyl cellulose alone and the microcapsules of the invention having an ethyl cellulose/palmitic acid shell wall, no significant differences were observed. When the dispersion rate of both types of microcapsules was observed, dispersion was complete within 20 min. in gastric fluid for both types of microcapsules. However, when a sample of microcapsules having a shell wall of ethyl cellulose was added to intestinal fluid, clumping or agglomeration of these microcapsules was observed. No such clumping or agglomeration was observed under the same conditions with the microcapsules of the present invention.

The microcapsules of the invention have more excellent free-flowing characteristics as compared with the microcapsules prepared using the ethyl cellulose alone. The incorporation of the amphiphile into the shell wall appears to aid in keeping the microcapsules of the invention from sticking to each other. This is an important feature as it adds to the ease of filling the microcapsules into gelatin capsules.

As described in Example 6, the mechanical strength of the microcapsules of the invention was compared to the prior art ethyl cellulose microcapsules.

EXAMPLE 6

Microcapsules having shell walls of ethyl cellulose were prepared as described in Example 5. A 5 g sample of these microcapsules was placed in a glass test tube and vortexed at high speed for 1 min. This procedure was repeated using a 5 g sample of the invention microcapsules prepared as described in Example 1. Thereafter, a sample of the ethyl cellulose microcapsules and a sample of the invention microcapsules which were not vortexed and a sample of each of the microcapsules which were vortexed were tested in the Dissolution Test described in Example 2 using SIF. After 1 hr., the appearance of potassium ion was assayed using the potassium electrode. The results are summarized in Table 5.

TABLE 5

| % K+ Released After 1 Hr. Shell Wall Type | | | |
|---|---|---|---|
| Et Cell | | Et/Palm. | |
| Non-Vortexed | Vortexed | Non-Vortexed | Vortexed |
| 20.6 | 27.8 | 13.7 | 13.3 |

As illustrated by the data summarized in Table 5, the shell walls of the invention did not break or rupture when exposed to high shear. Some breakage or rupturing of the prior art microcapsules did occur after exposure to mechanical shear as evidenced by the increased presence of potassium ion in the SIF.

The above result was confirmed by a "taste test." Immediately after the samples of microcapsules were vortexed, a small sample was placed on the tongue of one of the inventors herein. A "salty" taste was detected from the vortexed ethyl cellulose microcapsules while no such taste was detected from the sample of the vortexed invention microcapsules. As a control, samples of both the invention and prior art microcapsules which were not vortexed were tasted; no salty taste was detected from these samples.

Slow release capsules containing the microencapsulated potassium salt of the invention may be prepared by filling the appropriate quantity of the above described microencapsulated potassium salt, preferably KCl mixture into gelatin capsules of suitable size and shape. A slow release capsule may contain the mixture of the appropriate quantity of the microencapsulated potassium salt as herein described, together with another active drug substance, diluents, and the like. The diluent may be used to achieve the appropriate concentration of the slow release composition within the unit dosage form.

The rate of release of potassium salt from the interior of the microcapsule may also be varied by altering the thickness of the shell wall material applied. By combining coated potassium salt having different time release characteristics, various release profiles of medicament over a period many hours from administration may be achieved.

In addition of potassium salts, other pharmacologically active agents (active drug substance) may be microencapsulated as described herein, both the pharmacologic nature of the active therapeutic ingredient and the dosage to be incorporated into the present slow release microcapsule shell wall are not critical. Examples of such pharmacologically active ingredients are nitrate compounds, vasodilators, salicylate and acetylsalicylate compounds, antibiotic substances, sulfonamide drugs; anti-cholinergic compounds, sedatives, tranquilizing and hypnotic agents, psychotropic mood elevating medicaments, anti-inflammatory steroid compounds, broncho-dilating agents, cardiotonic agents, cardio-antiarrhythmic agents, water-soluble ionic metabolies and vitamins. Other medicaments requiring frequent repeated dosage administration by the oral route to maintain a therapeutically active blood level are particularly suitable for inclusion into the present slow release composition. Thus it will be seen that the scope of utility of the microcapsules of the invention are not limited to one particular active ingredient neither is the slowed release action achieved with only one class of active therapeutic compound, but arises from the properties of the microcapsule shell wall.

It is understood that changes and variations may be made from the foregoing embodiments of the present invention without departing from the spirit and scope thereof as defined in the appended claims.

What is claimed is:

1. A pharmaceutical composition comprising a microencapsulated potassium salt encapsulated in a shell wall consisting essentially of from about 85% to about 97% ethyl cellulose and from about 3% to about 15% of an amphiphile based on the weight of the shell wall; wherein the weight of said shell wall is from about 3% to about 15% of the total weight of said microencapsulated potassium salt.

2. A composition according to claim 1 wherein said salt is potassium chloride.

3. A composition according to claim 2 wherein said amphiphile is a $C_{12-20}$ fatty acid.

4. A composition according to claim 3 wherein said amphiphile is lauric acid, myristic acid, palmitic acid, stearic acid and arachidic acid.

5. A composition according to claim 4 wherein said amphiphile is selected from the group consisting of myristic and palmitic acid.

6. A composition according to claim 1 wherein in said shell wall, ethyl cellulose is present at from about 85% to about 95% based on the weight of the shell wall.

7. A composition according to claim 6 wherein said ethyl cellulose is present at about 89% to about 91% based on the weight of the shell wall.

8. A composition according to claim 7 wherein said ethyl cellulose is present at 91%.

9. A composition according to claim 7 wherein in said shell wall said amphiphile is present from about 8.5% to about 9.5% based on the weight of the shell wall.

10. A composition according to claim 9 wherein said amphiphile is present at about 9%.

11. A composition according to claim 1 contained in a gelatin capsule.

12. A composition according to claim 1 wherein the weight of said shell wall is from about 7% to about 13% of the total weight of said microencapsulated potassium salt.

13. A composition according to claim 11 wherein the weight of said shell wall is from about 8.5% to about 9.5%.

14. A composition according to claim 12 wherein the weight of said shell wall is about 9%.

15. Microencapsulated potassium salt wherein said microcapsule shell wall consists essentially of from about 85% to about 97% ethyl cellulose and from about 3% to about 15% of an amphiphile based on the weight of the shell wall; wherein the weight of the shell wall is from about 3% to about 15% of the total weight of the microencapsulated potassium salt.

16. Microencapsulated potassium salt according to claim 15 wherein said salt is potassium chloride.

17. Microencapsulated potassium chloride according to claim 16 wherein said amphiphile is lauric acid, myristic acid, palmitic acid, stearic acid and arachidic acid.

18. Microencapsulated potassium chloride according to claim 17 wherein said amphiphile is myristic acid or palmitic acid.

* * * * *